United States Patent [19]

Martens et al.

[11] 4,143,553
[45] Mar. 13, 1979

[54] CONTOURED SEARCH UNIT FOR DETECTING INTERNAL FLAWS

[75] Inventors: George D. Martens, New Milford; T. B. Hendricks, Bethel, both of Conn.

[73] Assignee: Automation Industries, Inc., Los Angeles, Calif.

[21] Appl. No.: 861,841

[22] Filed: Dec. 19, 1977

[51] Int. Cl.² .......................................... G01N 29/00
[52] U.S. Cl. .......................................... 73/625; 73/641
[58] Field of Search ................. 73/636, 624, 625, 620, 73/622, 641

[56] References Cited
U.S. PATENT DOCUMENTS

| 3,741,003 | 6/1973 | Gunkel ............................. 73/641 X |
| 3,837,202 | 9/1974 | Hetherington et al. ........... 73/641 X |

Primary Examiner—Jerry W. Myracle
Attorney, Agent, or Firm—Parmelee, Johnson, Bollinger & Bramblett

[57] ABSTRACT

A search unit for detecting internal flaws in the web of a railroad rail includes a plastic polymer shoe having a base surface contoured to conform generally to the web surface and of sufficient width to extend substantially across the width of the web. A plurality of dual ultrasonic transducers, each transducer including a transmitter and a spaced receiver, form a linear array across the width of the shoe and are angled with respect to each other. A couplant fluid is injected between the shoe and the rail web through fluid inlets in the shoe as the unit is slid along the rail.

15 Claims, 6 Drawing Figures

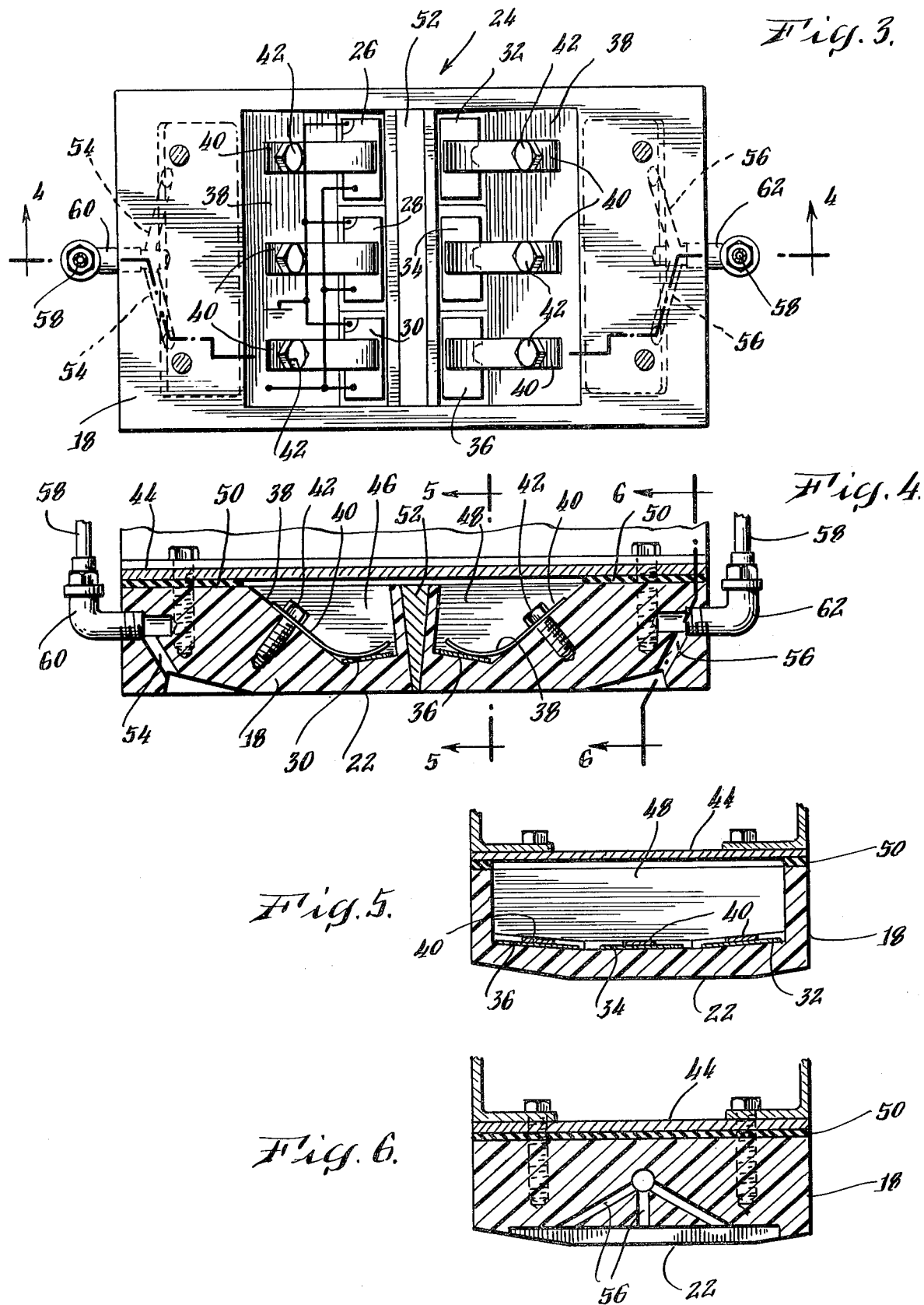

CONTOURED SEARCH UNIT FOR DETECTING INTERNAL FLAWS

BACKGROUND OF THE INVENTION

This invention relates to ultrasonic testing of elongated workpieces such as railroad rails. More particularly, it relates to the testing of unlaid rails as opposed to the testing of rails in track.

A common flaw found in railroad rails, particularly the first rail produced from an ingot, is an open seam within the web of the rail. The flaw, being a longitudinal separation within the web, is often referred to as "pipe." Such flaws cause welding problems which delay production. They also weaken the load supporting web of a rail. Rails having the flaws are rejected for the sake of safety and in order to avoid welding delays and future costs of replacement.

As pipe flaws are generally totally enclosed within the rail web, they cannot generally be detected by mere visual inspection. However, ultrasonic inspection devices have been used. In these devices, an ultrasonic signal is transmitted from a transducer and the reflection of the ultrasonic signal is detected. The detection may be by the ultrasonic transmitting crystal or by another spaced crystal. If the signal is reflected by a flaw before it reaches the back surface of the rail web, the reflection signal received at the receiver will be advanced in time from that ordinarily received from the back surface. A monitor detects the change in the received signal and indicates a flaw in the rail web.

The ultrasonic transducer is generally mounted in a small search unit which has a very limited inspection region because of the necessity to maintain adequate coupling to a concave surface. Accordingly, it must be passed ("scrubbed") up and down the height of the web as well as along the length of the web. Also, the web surface is not parallel with the web center plane across the height of the web which is the major flaw plane. Subsequently, ability to detect a flaw decreases as the angle between the transducer and the flaw plane of the web increases with movement of the transducer toward the rail head or base.

SUMMARY

An advantage of the present invention is that internal flaws in a workpiece such as a rail web can be detected by a single unidirectional pass of a search unit.

Another advantage of the present invention is that there are minimal variations in flaw detectability due to the web contour.

In accordance with one aspect of the invention, a search unit includes a shoe having a base surface dimensioned to span the workpiece and more specifically of a width about the same as the height of the web and contoured to conform generally to the web surface. A plurality of ultrasonic transducers are arranged in an array across the width of the shoe so that the entire web may be inspected with a single sweep of the search unit and the web contour covered by each transducer remains substantially constant.

According to other aspects of the invention, the ultrasonic transducers are positioned along a back surface of the shoe and are angled relative to each other so that ultrasonic signals transmitted by the angled transducers and refracted at the interface between the shoe and web continue through the web more nearly parallel until reflected within the web or at the back surface.

According to another aspect of the invention, each ultrasonic transducer is a dual transducer including a transmitter and a receiver angled relative to each other and having a sound absorbing buffer region therebetween.

According to other aspects of the invention, the shoe is formed of a wear-resistant plastic and includes a fluid inlet therein for introducing an ultrasonic couplant fluid between the shoe and web.

Internal flaws in the web are detected by scanning the web by sliding the shoe unidirectionally therealong. An ultrasonic signal is transmitted by the transmitter and the reflected signal is detected by the receiver. A detected signal before the back reflection indicates an internal flaw in the web.

BRIEF DESCRIPTION OF THE DRAWINGS

The foregoing and other objects, features, and advantages of the invention will be apparent from the following more particular description of a preferred embodiment of the invention, as illustrated in the accompanying drawings in which like reference characters refer to the same parts throughout the different views. The drawings are not necessarily to scale, emphasis instead being placed upon illustrating the principles of the invention.

FIG. 3 is a cross-sectional view of the shoe and transducer array taken substantially along the line 3—3 of FIG. 2;

FIG. 4 is a cross-sectional view, of the lower portion of the search unit, taken substantially along the line 4—4 of FIG. 3;

FIG. 5 is a sectional view of the search unit of FIG. 4 taken substantially along line 5—5; and FIG. 6 is a sectional view of the search unit of FIG. 4 taken substantially along line 6—6.

DESCRIPTION OF A PREFERRED EMBODIMENT

Figure 1:
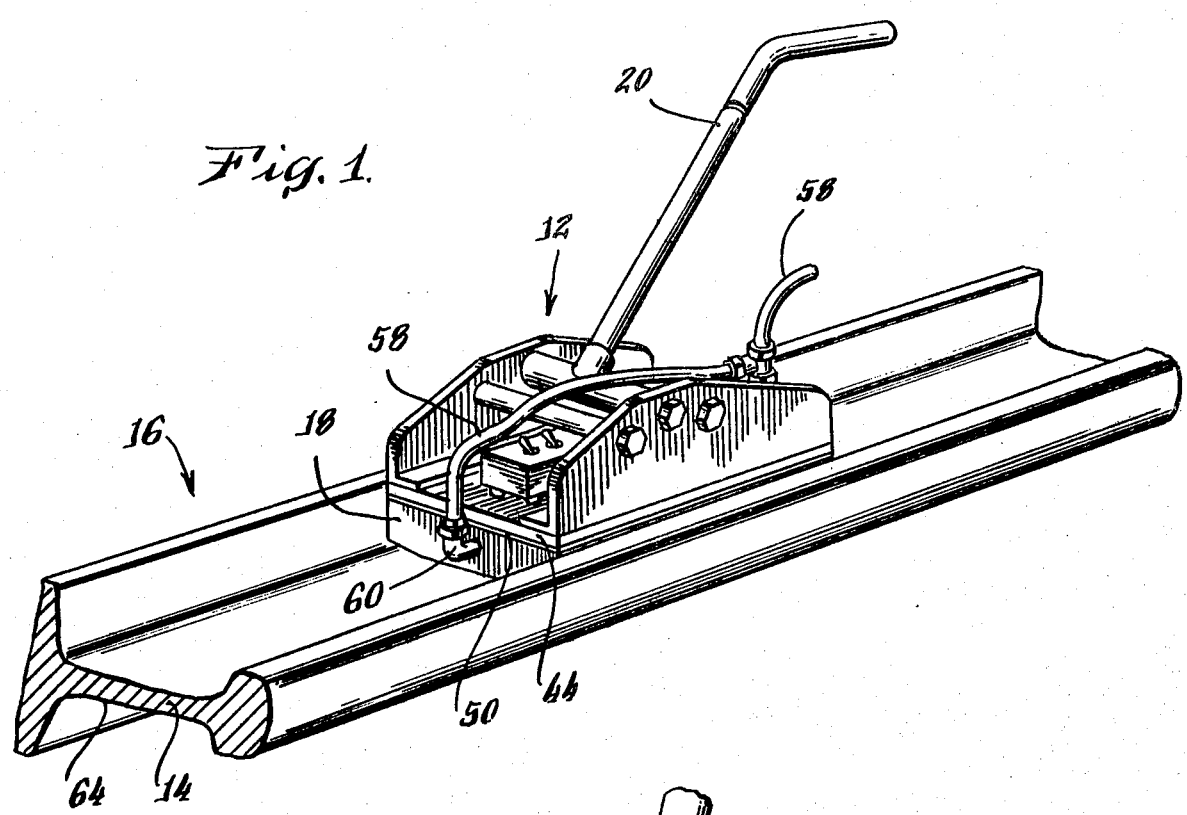
FIG. 1 is a perspective view of a search unit embodying the present invention positioned against the web of a railroad rail tilted on its side.
Figure 2:
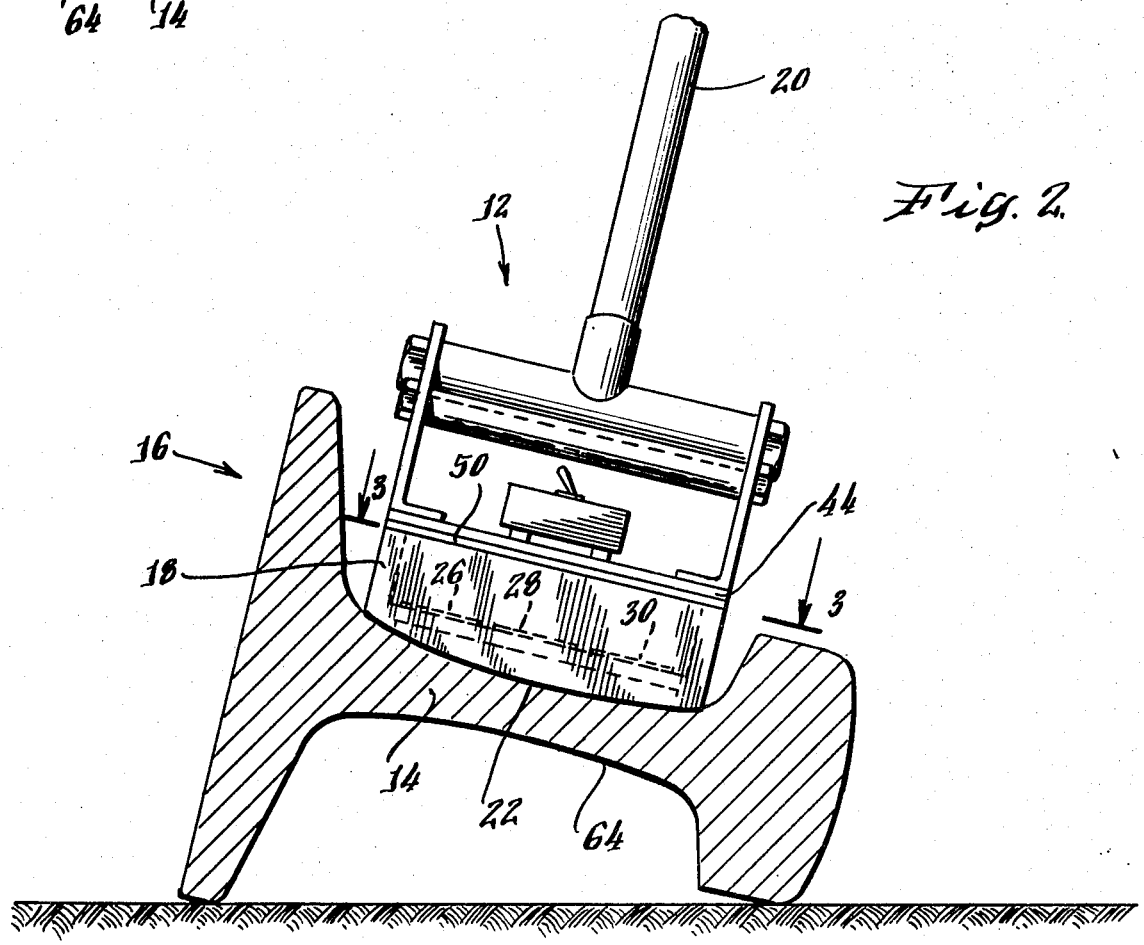
FIG. 2 is a front view of the search unit and rail shown in FIG. 1.

An ultrasonic search unit is shown generally at 12 in FIGS. 1 and 2. The unit is positioned against the web 14 of a railroad rail 16. For testing, the rail is positioned on its side as shown. A shoe 18 of the unit is adapted to slide longitudinally along the web when manually pushed by means of a handle 20.

The base surface 22 of the shoe 18 has a width about the same as the height of the web. The surface 22 is not flat; but rather, it is contoured to conform generally to the web surface. As shown, in FIGS. 5 and 6, the base surface 22 is formed of three planar portions angled with respect of each other. The angles between the planar portions are determined by the curve of the web across its width. The base surface 22 is finally shaped to the contour of the web of a rail of given size by means of sandpaper or emery cloth, or the equivalent. The contour of the base surface serves two purposes. First, the search unit is more readily maintained along a single scan line along the web. As will be set forth in more detail subsequently, the ultrasonic transducers in the search unit are aligned relative to the web contour and it is thus important that the transducers be properly positioned over respective predetermined segments of the web. Secondly, the contoured base surface of the shoe 18 minimizes the open space between the shoe 18 and the web and thus permits better acoustic coupling between the search unit and the rail.

As shown in FIG. 3, ultrasonic signals are transmitted and received by a linear array of dual transducers 24 extending across the width of the search unit. The array includes three ultrasonic transmitters, piezoelectric crystals 26, 28 and 30, and three ultrasonic receivers, piezoelectric crystals 32, 34 and 36. Because air backed crystals transmit a more powerful signal than do crystals which are potted, the crystals are held in place on the back surface 38 of the shoe 18 by leaf springs 40. The leaf springs are held to the shoe 18 by bolts 42. A back plate 44 is positioned over the transducer array to enclose the transmitters in a transmitter cavity 46 and the receivers in a receiver cavity 48. The cavities are hermetically sealed by a gasket 50.

In order that the only transmitted signals received by the receiver crystals are those signals reflected from the rail web, a sound absorbing region 52 is provided between the array of transmitters and the array of receivers. Any signals reflected toward the receivers at the interface between the shoe and web are absorbed in this region. Although the region might simply be an air cavity, it is filled with some sound absorbing plastic foam or the like in order to prevent couplant fluid from entering the shoe.

In order to provide more efficient ultrasonic coupling between the shoe 18 and the web 14, a couplant fluid is injected between the two through inlets 54 and 56 in the shoe. The couplant fluid, which may be water, is supplied through hoses 58 connected to the shoe fluid inlets by pipe couplings 60 and 62.

In operation, the search unit is manually pushed along the length of a rail with the shoe 18 placed against the web of the rail, and couplant fluid is introduced between the shoe 18 and web 14 through the inlets 54 and 56. Suitable electrical signals are applied to the transmitter transducers 26, 28 and 30 to generate ultrasonic signals which are transmitted through the shoe 18 and into the web. At least a portion of the ultrasonic signals is reflected by the back surface 64 of the web. These signals are reflected toward the receiver crystals 32, 34 and 36. To this end, the transmitters and receivers are angled with respect to each other as shown in FIG. 4. For transducers positioned about ⅜ of an inch from the base surface 22 of the shoe 18, the transducer crystals are angled about 6 degrees from the horizontal. Signals which impinge on the receiver crystals are detected by suitable monitoring circuitry which provides an indication of internal flaws in the web in accordance with the detected signals.

As the search unit is pushed along the web, a linear segment of the web is scanned by each dual transducer. Hence, with a single unidirectional movement, the entire web is completely scanned for internal flaws.

Due to the contour of the web surface, an ultrasonic signal directed perpendicular to a center line across the width of the web would be somewhat refracted at the interface between the shoe 18 and the web. Thus, for example, a signal transmitted by piezoelectric crystal 26 would be refracted toward crystal 34, thereby reducing the signal received by crystal 32 and increasing that received by crystal 34. Similarly, the signal transmitted by crystal 30 would be refracted toward crystal 34. In order to avoid this objectionable result, the outer crystals in the array are angled with respect to the center crystals. Thus, signals refracted at the interface continue more nearly parallel to each other. Reflected signals are similarly refracted. Accordingly, crystals 26 and 32 are mounted at a 1° angle with respect to the horizontal as shown in FIG. 5, and crystals 30 and 36 are angled at 2° with respect to the horizontal. These angles may vary with web contour and the acoustic velocity of the shoe.

Preferably, the search unit shoe 18 is formed of a wear-resistant plastic such as ultra high molecular weight polyethylene or acetal resin. These plastic polymers are exceptionally durable and have very low coefficients of friction. Further, they are not affected by moisture. A suitable acetal resin is sold under the trademark "Delrin."

The above described search unit is exceptionally durable and provides an accurate indication of internal web flaws with but a single pass of the unit along the rail. Inaccuracies in the received signal due to refraction or reflection at the shoe/web interface are substantially avoided.

While the invention has been particularly shown and described with reference to a preferred embodiment thereof, it will be understood by those skilled in the art that various changes in form and details may be made therein without departing from the spirit and scope of the invention as defined by the appended claims.

What is claimed is:

1. An ultrasonic search unit for detection of internal flaws in an elongated workpiece having a curved contour by sliding said shoe in a single pass along the length of said workpiece, said search unit comprising:
   a shoe with a base surface dimensioned to span the workpiece and conforming generally to the contour of the workpiece, said shoe being adapted to be slid along the length of said workpiece; and
   a plurality of transducers for transmitting ultrasonic signals into said workpiece and for receiving signals reflected from within said workpiece, said transducers being arranged in an array across said shoe, said transducers being angled relative to each other, the angles of said transducers being set such that the signals transmitted by said transducers are refracted at the interface between said shoe and said workpiece and the refracted signals continue through said workpiece more nearly parallel to each other.

2. The search unit of claim 1 wherein said transducers are positioned along a back surface of said shoe opposite to said base surface and said signals are transmitted through said shoe into said workpiece and signals reflected from within said workpiece return to said transducers through said shoe.

3. The search unit of claim 1 wherein each of said transducers is a dual transducer comprising a transmitter and a receiver spaced from said transmitter, said transmitter and said receiver being angled relative to each other so that signals transmitted from said transmitter and reflected within said workpiece are intercepted by said receiver.

4. The search unit of claim 3 wherein said shoe includes a sound absorbing buffer region between said transmitters and receivers wherein signals reflected from said interface toward said receiver are absorbed.

5. The search unit of claim 1 wherein said shoe includes a couplant fluid inlet for introducing an ultrasonic couplant fluid between said shoe and said workpiece.

6. The search unit of claim 1 wherein said shoe is formed of a plastic polymer.

7. The search unit of claim 6 wherein said shoe is formed of polyethylene.

8. The search unit of claim 1 wherein each of said transducers is a dual transducer comprising a transmitter and a receiver spaced from said transmitter, said transmitter and said receiver being angled relative to each other so that signals transmitted from said transmitter and reflected within said workpiece are intercepted by said receiver.

9. The search unit of claim 8 wherein said shoe includes a sound absorbing buffer region between transmitters and receivers wherein signals reflected from said interface toward said receiver are absorbed.

10. An acoustic search unit for detection of internal flaws in the web of a railroad rail, said search unit comprising:

a shoe formed of a plastic polymer with a base surface having a width about the same as the height of said web and conforming generally to the web surface, said shoe being adapted to be slid along the length of said web, and a plurality of acoustic transducers for transmitting acoustic signals into said web and for receiving signals reflected from within said web, said transducers being arranged in an array across the width of said shoe along a back surface of said shoe opposite to said base surface and being angled relative to each other, the angles of said transducers being set such that the acoustic signals transmitted by said acoustic transducers through said shoe and into said web are refracted at the interface between said shoe and said web and the refracted signals continue through said web more nearly parallel to each other until reflected within said web, each of said acoustic transducers being a dual transducer comprising an acoustic transmitter and an acoustic receiver spaced from said transmitter, said transmitter and said receiver being angled relative to each other so that acoustic signals transmitted from said transmitter and reflected within said web are detected by said receiver, said shoe including a sound absorbing buffer region between said transmitters and said receivers wherein signals reflected from said interface toward said receiver are absorbed.

11. The search unit of claim 10 wherein said shoe includes a couplant fluid inlet for introducing an acoustic couplant fluid between said shoe and said web.

12. The method of detecting internal flaws in the web of a railroad rail, said method comprising:

scanning said web by unidirectionally sliding a search unit therealong, said search unit comprising a shoe having a base surface of a width about the same as the height of said web and conforming generally to the web surface and a plurality of acoustic transducers arranged in an array across the width of said shoe, generating an acoustic signal by means of said acoustic transducer and transmitting said signal into said web, detecting those signals reflected from within said web, and providing an indication of internal flaws in said web in accordance with the detected signals.

13. The method of claim 12 for detecting internal flaws wherein said transducers are angled relative to each other, the angles of said transducers being set such that the acoustic signals transmitted by said acoustic transducers into said web are refracted at the interface between said shoe and said web and the refracted signals continue through said web more nearly parallel to each other.

14. The method of claim 12 for detecting internal flaws wherein each of said acoustic transducers is a dual transducer comprising an acoustic transmitter and an acoustic receiver spaced from said transmitter, said transmitter and said receiver being angled relative to each other so that acoustic signals transmitted from said transmitter and reflected within said web are detected by said receiver.

15. The method of claim 12 for detecting internal flaws wherein said scanning includes introducing couplant fluid between said shoe and said web.

* * * * *